US006411434B1

United States Patent
Eastman et al.

(10) Patent No.: US 6,411,434 B1
(45) Date of Patent: Jun. 25, 2002

(54) CASSETTE FOR FACILITATING OPTICAL SECTIONING OF A RETAINED TISSUE SPECIMEN

(75) Inventors: Jay M. Eastman, Pittsford; William J. Fox, Rochester; Roger J. Greenwald, Holley; Kevin P. Roesser, Rochester; James M. Zavislan, Pittsford, all of NY (US)

(73) Assignee: Lucid, Inc., Rochester, NY (US)

( * ) Notice: Subject to any disclaimer, the term of this patent is extended or adjusted under 35 U.S.C. 154(b) by 0 days.

(21) Appl. No.: 09/502,252

(22) Filed: Feb. 17, 2000

Related U.S. Application Data (60) Provisional application No. 60/120,534, filed on Feb. 17, 1999.

(51) Int. Cl.[7] .......................... G02B 21/34; G01N 21/01
(52) U.S. Cl. ........................................ 359/398; 356/246
(58) Field of Search ................................ 359/396, 397, 359/398; 356/246

(56) References Cited

U.S. PATENT DOCUMENTS 3,031,924 A * 5/1962 Lamal ......................... 359/398
3,510,194 A * 5/1970 Connelly .................... 359/398

(List continued on next page.)

FOREIGN PATENT DOCUMENTS

WO     WO 96/21938     7/1996

OTHER PUBLICATIONS

Rajadhyaksha, M. et al., Confocal Laser Microscope Images Tissue In Vivo, Laser Focus World, Feb. 1997, pp. 119–127.
Rajadhyaksha, M. et al., In Vivo Confocal Scanning Laser Microscopy of Human Skin: Melanin Provides Strong Contrast, The Journal of Investigative Dermatology, Jun. 1995, vol. 104, No. 6, pp. 946–952.
Gross, Kenneth G. et al., Mohs Surgery, Fundamentals and Techniques, 1999, p. 94.
Schmitt, Joseph M. et al., Optical Characterization of Dense Tissues Using Low–coherence Interferometry, 1993, SPIE vol. 1889, pp. 197–211.

* cited by examiner

Primary Examiner—Mark A. Robinson
(74) Attorney, Agent, or Firm—Kenneth J. LuKacher (57) ABSTRACT

A cassette for retaining a specimen of surgically exposed tissue from a patient in an orientation that facilitates optical sectioning of the tissue by a confocal microscopic or other optical imaging microscope. The cassette includes a base member having a rigid optically transparent window upon which a tissue specimen is situated, a pliable membrane locatable over a substantial portion of the base member including the window, and an upper member, having an aperture therethrough, which can cover the base member to provide an enclosed cavity between the membrane and the window sealing the tissue specimen therein. With the tissue specimen in the enclosed cavity of the cassette, the edges of the tissue specimen may be positioned planar against the window and retained in that position by bonds formed between the membrane and window at multiple points or locations around the tissue specimen. The specimen retained in the cavity is viewable through the aperture of the upper member and imagible by a confocal microscope, or other optical imaging microscope, through the window of the base member. The base member has an injection port through which fluid may be inserted and removed from the cavity of the cassette in which the tissue specimen is retained. Such fluids can facilitate imaging of the specimen by an optical imaging microscope, or can be used to place the specimen in a preservative for archival purposes. A label with indicia identifying the tissue specimen may be applied to the cassette. The cassette may be part of a confocal imaging system to produce microscopic images of sections of the tissue specimen useful for Mohs surgery.

51 Claims, 8 Drawing Sheets

U.S. PATENT DOCUMENTS

| | | | |
|---|---|---|---|
| 3,551,023 A | * 12/1970 | Brackett | |
| 3,556,633 A | 1/1971 | Mutschmann et al. | |
| 4,208,101 A | 6/1980 | Trapp et al. | |
| 4,752,347 A | 6/1988 | Rada | 156/382 |
| 4,965,441 A | 10/1990 | Picard | 250/201.3 |
| 4,974,952 A | 12/1990 | Focht | |
| 5,034,613 A | 7/1991 | Denk et al. | 250/458.1 |
| 5,120,953 A | 6/1992 | Harris | 250/227.2 |
| 5,122,653 A | 6/1992 | Ohki | 250/216 |
| 5,503,741 A | 4/1996 | Clark | 210/232 |
| 5,532,874 A | 7/1996 | Stein | 359/394 |
| 5,719,700 A | 2/1998 | Corcuff et al. | 359/368 |
| 5,788,639 A | 8/1998 | Zavislan et al. | 600/476 |
| 5,812,312 A * | 9/1998 | Lorincz | 359/397 |
| 5,836,877 A | 11/1998 | Zavislan | 600/407 |
| 5,870,223 A | 2/1999 | Tomimatsu | 359/392 |
| 5,880,880 A | 3/1999 | Anderson et al. | 359/385 |
| 5,995,283 A | 11/1999 | Anderson et al. | 359/385 |
| 6,048,723 A * | 4/2000 | Banes | 435/305.1 |
| 6,330,106 B1 | 12/2001 | Greenwald et al. | 359/398 |

* cited by examiner

CASSETTE FOR FACILITATING OPTICAL SECTIONING OF A RETAINED TISSUE SPECIMEN

This application claims the benefit of priority to U.S. Provisional Application No. 60/120,534, filed Feb. 17, 1999, which in herein incorporated by reference.

FIELD OF THE INVENTION

The present invention relates to a cassette for retaining a tissue specimen, and relates particularly to a cassette for retaining a specimen of surgically exposed tissue from a patient in an orientation that facilitates optical sectioning of the tissue by a confocal microscope, or other optical imaging microscope, for Mohs micrographic surgery. The invention further relates to a method of using the cassette for preparing a tissue specimen for examination by a confocal microscope or other optical imaging microscope, and a system for optically sectioning a tissue specimen retained in a cassette.

BACKGROUND OF THE INVENTION

In Mohs micrographic surgery, tissue having a tumor, typically a carcinoma on the skin of the head or neck, is excised from a patient under microscopic control. The excised tissue specimen, often called a biopsy, is horizontally sliced to provide tissue sections which are then histologically prepared on slides. The slides are reviewed under a microscope to determine whether the tumor is fully contained in the excised tissue. This is indicated by the absence of the tumor in the edges or margins of the excised tissue. If the tumor is not fully contained in the excised tissue, additional tissue from the patient is excised and the procedure repeated until all tissue sections taken indicate the tumor has been removed from the patient. Mohs surgery permits removal of a tumor with maximum preservation of normal surrounding tissue. Mohs surgery is described in the book entitled MOHS SURGERY FUNDAMENTALS AND TECHNIQUES (Kenneth G. Gross, M.D. et al. eds., 1999).

To prepare each tissue specimen in Mohs surgery, multiple sections or slices are manually made with a microtome, where each section is planar and parallel to each other. Often the tissue specimen is first frozen to make the tissue easier to manipulate and cut by the microtome. However, since numerous sections must be made from each tissue specimen and then histologically prepared on slides, this procedure is both tedious and time consuming.

U.S. Pat. No. 4,752,347 provides a method and apparatus for preparing a tissue specimen for sectioning for Mohs surgery. The patent describes placing an excised tissue specimen on a platform, applying a flexible plastic membrane over the tissue specimen, and evacuating the area between the membrane and the tissue specimen. This retracts the membrane onto the platform and pushes the edges of the tissue specimen into a planar orientation parallel to the platform. While under the pressure of the membrane, the tissue sections may be manipulated by an operator through the membrane until the desired orientation is obtained. The edges of the tissue specimen are thus oriented to flatten the edges of the specimen down. The specimen is then frozen, peeled away from the platform, and sectioned by a microtome. Since the edges of the specimen are oriented planar when sectioned by the microtome, a single section can be made having the edges of interest in Mohs surgery. This procedure is adequate for obtaining a section which can be placed on a slide for review under a microscope, but is not useful with optical imaging techniques, such as provided by confocal microscopes, which can examine a surgically exposed tissue specimen without the need for traditional microtome sectioning or slide preparation.

Confocal microscopes optically section naturally or surgically exposed tissue to produce microscopic images of tissue sections. An example of a confocal microscope is the "VivaScope" manufactured by Lucid Inc. of Henrietta, N.Y. Other examples of confocal microscopes are described in U.S. Pat. No. 5,788,639, published International Patent Application WO 96/21938, and in articles by Milind Rajadhyaksha et al., "In vivo Confocal Scanning Laser Microscopy of Human Skin: Melanin provides strong contrast," The Journal of Investigative Dermatology, Volume 104, No. 6, June 1995, and Milind Rajadhyaksha and James M. Zavislan, "Confocal laser microscope images tissue in vivo," Laser Focus World, February 1997, pages 119–127. Further, optically sectioned microscopic images of tissue can be produced by optical coherence tomography or interferometry, such as described in Schmitt et al., "Optical characterization of disease tissues using low-coherence interferometry," Proc. of SPIE, Volume 1889 (1993), or by a two-photon laser microscope, such as described in U.S. Pat. No. 5,034,613.

One problem with optical imaging of a tissue specimen for Mohs surgery is that the tissue specimen is generally too thick, for example 2–3 mm, to enable optically imaging of the edges of the specimen to determine if the specimen contains all of the tumor. Typically, a confocal microscope is limited to producing adequate images of tissue sections at 100–200 microns. Thus, it would be desirable to optically image a tissue specimen in which the edges of the tissue specimen are oriented planar against an optically transparent surface through which the specimen can be optically sectioned.

In addition, optical imaging systems, such as confocal microscopes, generally require the use of a liquid immersion objective lens directed toward the tissue specimen. This necessitates that the tissue specimen be wetted or immersed in a fluid having an optical index suitable for the objective lens, otherwise, the imaging performance of the system is severely degraded. It is thus also desirable that fluids maybe insertable to a properly oriented tissue specimen, and further removable, such that the fluid may be replaced with another fluid to change the imaging characteristics of the tissue.

Although U.S. Pat. No. 4,752,347 describes positioning the edges of a tissue specimen planar on a platform under a plastic membrane held by vacuum to the platform, the tissue specimen described in this patent is mechanically sectioned, rather than optically sectioned. Further, prior to mechanical sectioning, such a specimen is incompatible with optical imaging techniques since fluid cannot be present with a tissue specimen in a vacuum, and the platform does not provide a surface through which optical imaging can be performed. For example, liquids under a vacuum would be suctioned away from the specimen, while gases, under the reduced pressure, would dissolve in any liquids to form bubbles, or such gases may boil or evaporate.

Furthermore, the traditional slides from tissue specimens produced by Mohs surgery must be archived for a minimum retention time in compliance with regulatory requirements, or to enable future reanalysis of the slides for legal purposes. This requires storage of the slides for many years which is cumbersome for large volumes of sectioned tissue specimens. Furthermore, each slide must be labeled in accordance with an identification system to facilitate locating the slides if they are ever needed.

In the area of dialysis, U.S. Pat. No. 5,503,741 describes a device having a sealed vacant chamber formed between two parallel dialysis membranes affixed to each side of a gasket. A needle may be inserted through the gasket to delivery or withdraw a sample from the chamber. The device is used for permitting dialysis, i.e., molecular exchange, between the sample in the chamber and an external solution. Such a device is limited to dialysis and provides no mechanism for retaining a tissue specimen in a planar orientation for optical sectioning.

SUMMARY OF THE INVENTION

Accordingly, it is the principal object of the present invention to provide a cassette for retaining a specimen of surgically exposed tissue from a patient which facilitates optical examination of the tissue by a confocal microscopic or other optical imaging microscope.

It is another object of the present invention to provide a cassette for retaining a tissue specimen in a cavity in which the edges of the tissue specimen can be positioned and retained in a planar orientation against an optically transparent surface It is still another object of the present invention to provide a cassette for retaining a tissue specimen in a cavity which allows fluid to be insertable and removable from the cavity containing the tissue specimen.

It is a further object of the present invention to provide a cassette for retaining a tissue specimen which enables Mohs surgery by optical sectioning the specimen with a confocal microscopic or other optical imaging microscope.

It is a still another object of the present invention to provide a cassette for a tissue specimen which can be used to archive and identify the tissue specimen more easily than the prior art tissue specimens from Mohs surgery which are physically sectioned and prepared on multiple slides.

It is yet another object of the present invention to provide a method for using a cassette to prepare a tissue specimen for examination by a confocal microscope or other optical imaging microscope.

A still further object of the present invention is to provide a cassette for retaining a tissue specimen which allows the entire sample to be observable in the cassette through the top and bottom of the cassette.

Briefly described, the present invention embodies a cassette having a base member with a rigid optically transparent window upon which a tissue specimen is situated, a pliable plastic membrane which is locatable over a substantial portion of the base member including the window, and an upper member, having an aperture therethrough, locatable over the base member to provide an enclosed cavity between the membrane and the window sealing the tissue specimen therein. With the tissue specimen in the cavity, the edges of the tissue specimen may be positioned through the aperture of the upper member and the membrane such that they lie planar against the window. The edges may be retained in that position by multiple bonds formed between the membrane and window at points or locations around the tissue specimen. The specimen is observable through the aperture of the upper member and imagible by an optical imaging microscope through the window of the base member.

The base member may has at least one injection port through which fluids, via a syringe needle, may be inserted and removed from the tissue specimen retained in the cavity of the cassette. Such fluids can facilitate imaging of the specimen by the optical imaging microscope, or can be used to place the specimen in a preservative for archiving purposes. A label with indicia identifying the tissue specimen may be applied to the cassette.

To form the cavity containing the tissue specimen, the lower surface of the upper member may have an adhesive, such as double-sided tape, which produces a seal between the upper and base members when the upper member is located over the base member. In another embodiment, the base member may have walls extending about its periphery into which the upper member may be received. The upper member has an annular ridge extending along its outer edge which is received in an annular grove along the inside of the wall of the base member, thereby forming a seal between the upper and base members.

When the cassette is closed, i.e., the tissue specimen is sealed in the cavity between the membrane and window, the membrane is held tightly by the upper member against the base member over the tissue specimen. The pressure of the membrane may compress the tissue specimen toward the window of the base member. The top of the tissue specimen can be cut or scored prior to closure of the cassette to facilitate movement of the edges of the tissue specimen toward the window when the specimen is compressed by the membrane. A user, such as a physician or trained operator, with a first probe may manipulate under the tension of the membrane each of the edges of the specimen planar against the window, and then with a second probe retain the edge in that planar position by bonding the membrane and window together at one or more points near the specimen's edge. To produce a bond at each point, the second probe pushes the membrane adjacent the window and then conducts heat to join the window and membrane together. Thus, the edges of the tissue specimen are oriented planar against an optically transmissive surface provided by the window of the cassette. Fluids can be inserted and removed from the tissue specimen through the injection port, since the multiple bonds do not seal the specimen within the cavity between the membrane and the window. Other bond actuating means may also be used such as sonic welding, or by the use of a contact, or UV cure, adhesive. Such an adhesive may be applied to lower surface of the membrane or upper surface of window facing the membrane, or both, prior to placement of the tissue specimen in the cassette, such that contact of the membrane and window by the second probe forms an adhesive bond.

The cassette having a properly oriented tissue specimen may be part of a confocal imaging system for producing microscopic images of sections of the tissue contained in the cassette. The system includes a confocal imaging head, a stage supporting the cassette which presents the window of the cassette to an objective lens of the confocal imaging head, and a camera which can capture images of the specimen through the aperture of the cassette's upper member. A control system is coupled to a display, the confocal imaging head and the camera to visualize on the display both images of microscope sections of the tissue specimen produced by the confocal imaging head and macroscopic images of the tissue captured by the camera. During examination of the tissue specimen in the cassette, the images from the camera can be used to identify the location of the microscopic images of sections with respect to the specimen.

The present invention further embodies a method using a cassette for preparing a tissue specimen for examination by a confocal microscope or other optical imaging microscope. The method includes the steps of locating a tissue specimen on a rigid optically transparent window of a base member, placing a pliable optically transparent membrane over at least a substantial portion of the base member including the window, sealingly engaging the membrane to the base member to produce a cavity between the membrane and the window, positioning edges of the tissue specimen against the window, and fixing the location of the edges positioned against the window by connecting the membrane to the window at multiple points.

BRIEF DESCRIPTION OF THE DRAWINGS

The foregoing objects, features and advantages of the invention will become more apparent from a reading of the following description in connection with the accompanying drawings, in which:

FIGS. 1 and 1A are perspective views of an open cassette in accordance with the present invention in which FIG. 1 shows the membrane attached to the upper member of the cassette, and FIG. 1A shows the membrane separate from the upper member of the cassette;

DETAILED DESCRIPTION OF INVENTION

Figure 1:
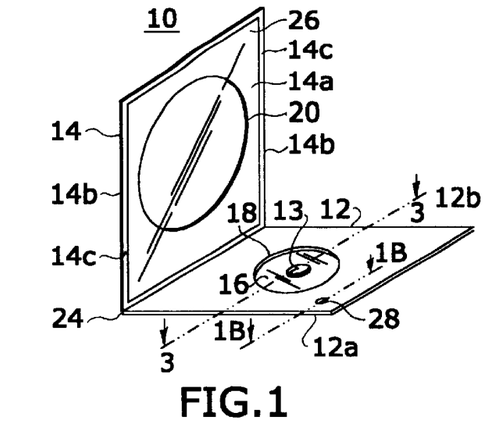
Figure 1A:
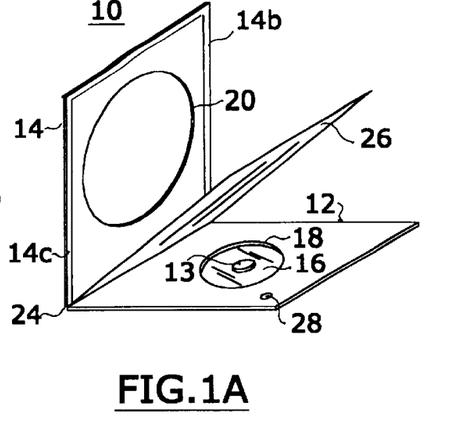
Figure 1B:
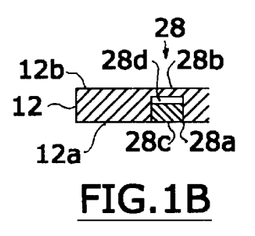
FIG. 1B is cross-sectional view along line 1B—1B of FIG. 1 showing the injection port of the cassette of FIG. 1 in more detail.
Figure 1C:
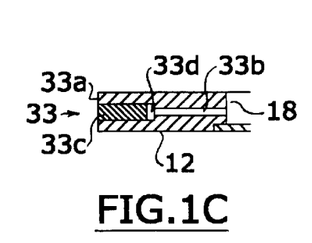
FIG. 1C is a partial cross-sectional view from the edge of the cassette along line 3—3 of FIG. 1 showing an alternative side injection port.
Figure 2:
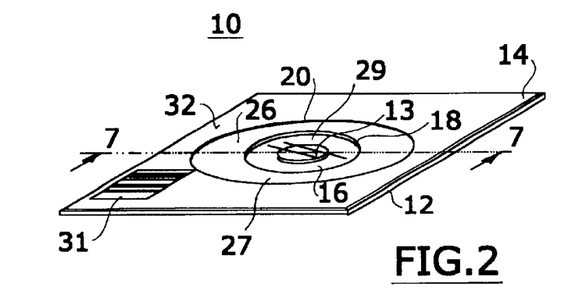
FIG. 2 is a perspective view of the cassette of FIG. 1 or FIG. 1A when closed.
Figure 3:
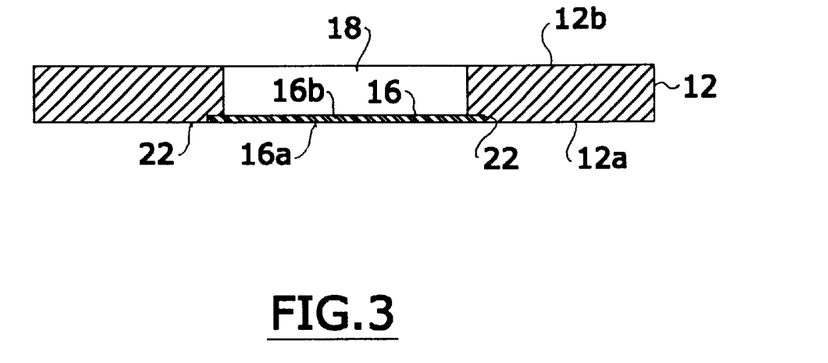
FIG. 3 is cross-sectional view along line 3—3 of FIG. 1 showing the window of the base member of the cassette without a tissue specimen.

Referring to FIGS. 1–3, a cassette 10 of the present invention is shown having a base member 12 and an upper member 14. Base member 12 has an aperture 18 and a rigid optically transparent window 16 situated in aperture 18. The upper member 14 has an aperture 20 preferably substantially greater in size than the aperture 18 of base member 12. Base and upper members 12 and 14 are hinged at a hinge 24 which allows cassette 10 to have an open state, as shown in FIG. 1, and a closed state, as shown in FIG. 2, where upper member 14 covers base member 12. Although preferably base and upper members 12 and 14 are attached by a hinge 24, they may, in the alternative, be separate and unattached to each other when cassette 10 is in an open state.

Figure 4:
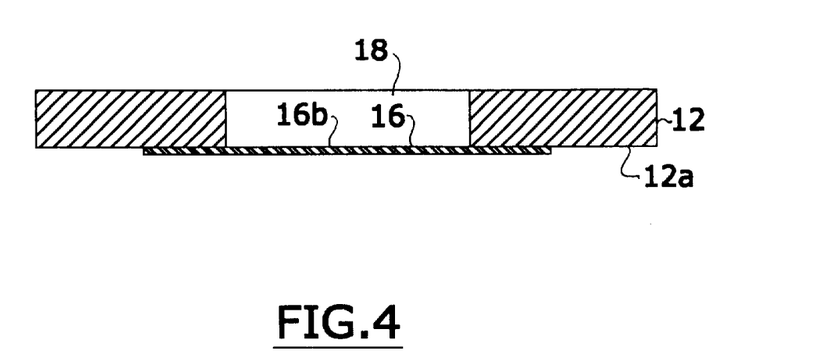
FIG. 4 is cross-sectional view along line 3—3 of FIG. 1 showing another embodiment of the window of the base member of the cassette without a tissue specimen.
Figure 5:
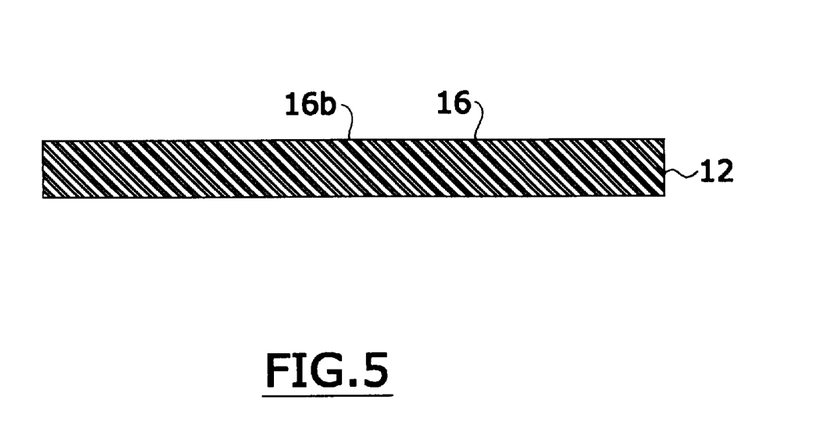
FIG. 5 is cross-sectional view along line 3—3 of FIG. 1 showing another embodiment of the base member without the tissue specimen in which the base member is composed of an optically transparent material to provide the window of the cassette when the cassette is closed.

As best shown in FIG. 3, at the bottom surface 12a of base member 12, the base member has an annular shelf 22 in communication with aperture 18. Window 16 is inset on shelf 22, such that bottom surface 12a of the base member is planar with the lower surface 16a of window 16. Window 16 may be held by an adhesive, such as glue, upon shelf 22, or may be insert molded with base member 12. In the alternative, window 16 may be attached to bottom surface 12a underneath aperture 18 without shelf 22, such as by an adhesive or glue along the part of bottom surface 12a which interfaces with window 16, as shown in FIG. 4. The window 16 may be composed of a cut out sheet of thin glass or amorphous polyolefin, such as Zeonex plastic, or other optically homogeneous material through which optical imaging can be performed. Preferably, window 16 is of 0.006 inch thick Zeonex plastic film which is rigidly attached to the base member 12 in either the configuration of FIGS. 3 or 4. The attachment of window 16 in cassette 10 should not be limited to that described herein. Any means for attaching an optical transparent window to form part of base member 12 may be used. The thickness of the window 16 depends on the working distance of the optical image system which will image the tissue specimen through the window. In a further alternative shown in FIG. 5, the base member 12 may itself be composed of an optically transmissive material, such as 1 millimeter thick Zeonex plastic, without aperture 18. Window 16 in FIG. 5 represents the part of the base member 12 below aperture 20 when the cassette 10 is in a closed state.

A pliable plastic membrane or film 26 (FIGS. 1 and 1A) is attached to bottom surface 14a of upper member 12, across aperture 20. Membrane 26 does not extend to the outer edge 14b of upper member 14, thereby leaving a region 14c near the outer edge of the upper member. An adhesive, such as double-sided tape, may fix membrane 26 to upper member 12 along bottom surface 14a outside region 14c. Optionally, membrane 26 may be separate from upper member 12, as shown in FIG. 1A, in which the membrane is held along one side by hinge 24. The membrane 26 may be, for example, a thin layer of plastic, such as plastic wrap typically used for food preservation, and should be sufficiently transparent to provide viewing therethrough by a user or camera.

Base member 12 further includes an injection port 28, as best shown in FIG. 1B. The injection port 28 is defined by an opening 28a which extends from the lower surface 12a of the base member 12 partially through the base member, a channel 28b which extends from the opening 28a to the upper surface 12b of the base member 12, and a self-sealing member 28c which is received in opening 28a from the bottom surface 12a of the base member. Between self-sealing member 28c and channel 28b is a passageway 28d in communication with channel 28b. Self-sealing member 28c may be composed of rubber, and may be similar to the self-sealing members used with medical vials for enabling a syringe needle to be inserted without loss of vial containment after removal of the syringe needle. An alternative side injection port 33 from the side of base member 12 is shown in FIG. 1C. Injection port 33 has an opening 33a partially through the base member, a channel 33b which extend from opening 33a to the wall of aperture 18, a self-sealing member 33c which is received in opening 33a, and a passageway 33d between the self-sealing member 33c and channel 33b. As will be described later, a syringe needle may be inserted into the injection port 28 or 33 through self-sealing member 28c or 33c to passageway 28d or 33d to insert or remove fluid from a cavity in the cassette 10 containing the tissue specimen, via channel 28b or 33b, when the cassette 10 is in a closed state. Although only one injection port is illustrated in FIGS. 1, 1B and 1C, multiple ones of the injection ports may be provided in cassette 10.

The base and upper members 12 and 14 may be composed of rigid material, such as plastic. Hinge 24 may also be made of plastic, or can be provided by a strip of adhesive material, such as tape, along the one side of members 12 and 14. Member 12 and 14, and hinge 24 may be a single molded piece, or separately molded. The dimensions of the cassette 10 are such that window 16 has a diameter larger than the width of the tissue specimen to be located on the window. For example, the cassette may have an aperture 18 having a 2 cm diameter and a 3 mm depth to window 16, and when closed the cassette may be 2.5 cm in length by 2.5 cm in width with a height of 7 mm. The cassette 10 may be larger than these dimensions to accommodate larger tissue specimens. Apertures 18 and 20 are circular, but may be rectangular, or other shape.

Figure 6:
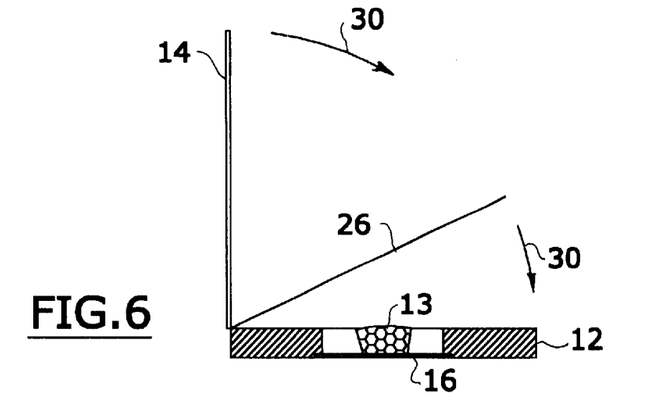
FIG. 6 is a cross-sectional view similar to FIG. 3 showing the movement of the upper member and the membrane over the base member of the cassette of FIG. 1A from an open cassette to a closed cassette.

In an open state, i.e., an open cassette 10, a surgically exposed tissue specimen 13 is situated on window 16, as shown for example in FIGS. 1 and 1A. Typically, the tissue specimen is elliptical in shape with curved, sloping sides. With the tissue specimen 13 on window 14, upper member 16 is located over the base member 12 to cover the base member, such that membrane 26 lies between the base member and upper member over aperture 18 of the base member. The cassette 10 in this closed state, i.e., a closed cassette, is shown for example in FIG. 2. In the example of FIG. 1A, FIG. 6 shows upper member 14 and membrane 26 rotating along an arc defined by hinge 24 to provide a closed cassette, as indicated by arrows 30.

Figures 7, 8:
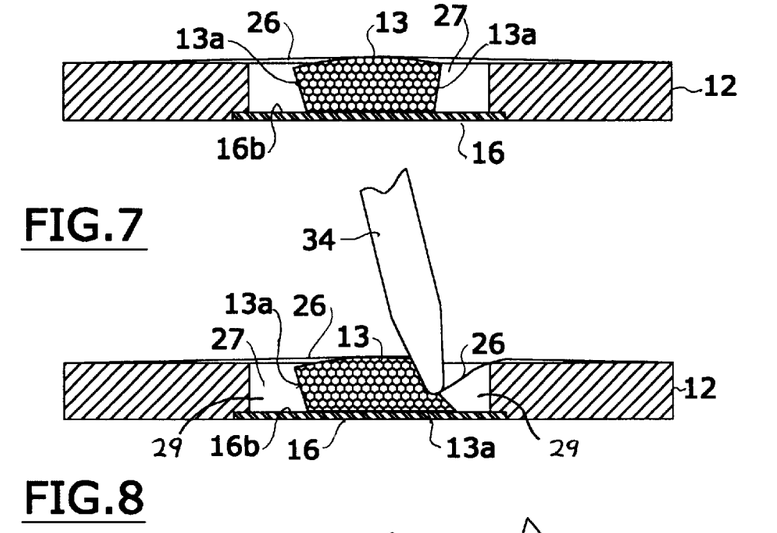
FIG. 7 is a cross-sectional view along line 7—7 of FIG. 2 showing the tissue specimen sealed in a cavity between the membrane and the window of the cassette.
FIG. 8 is a cross-section view similar to FIG. 7 showing an example of a first probe positioning an edge of the tissue specimen in a planar orientation against the window of the cassette.

In a closed state, a hermetic seal is formed between the upper member 14 and base member 12 to define an enclosed cavity or compartment 27 between the membrane 26 and window 16 containing tissue specimen 13 (FIGS. 2 and 7). The seal may be provided by an adhesive, such as double-sided tape, along the region 14c of upper member 14 (FIGS. 1 and 1A). The seal may also be provided by region 14c of upper member 14 having a continuous raised ridge which may be received is a corresponding continuous groove on the top surface 12b of the base member 12, such that the raised ridge of the upper member snap fits in the groove of the base member. Other sealing means may alternatively be used, such as a gasket between the upper and base members, UV cure adhesive, sonic welding, or thermal welding.

Figure 11:
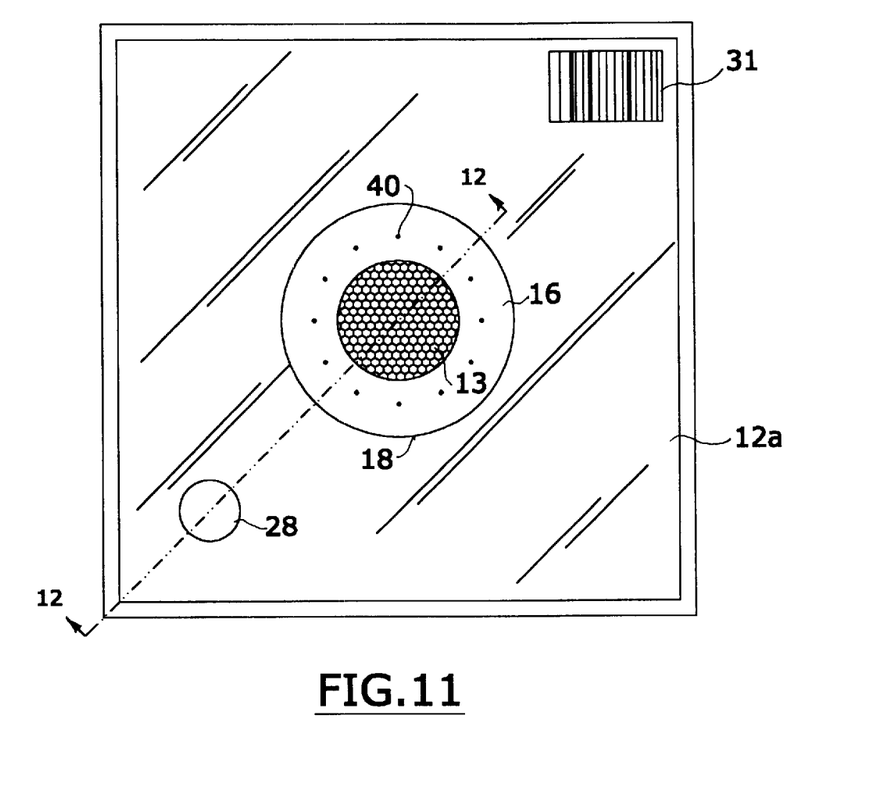
FIG. 11 is a bottom view of the cassette of FIG. 10 showing the injection port of the cassette and an example of a tissue specimen in the cassette with the edges of the specimen positioned planar against the window by multiple bonds at locations around the tissue specimen.

In the closed cassette, the tissue specimen 13 is observable through both window 14, and membrane 26 through aperture 20 of upper member 14. Although aperture 20 is preferably larger than aperture 18, it may be the same size or smaller than aperture 18 so long as when the cassette is closed both the tissue specimen 13 a gap or space 29 (FIG. 2) is viewable around the edges 13a of the tissue specimen through aperture 20. Further, with the tissue specimen 13 sealed in cavity 27, the injection port 28 (and/or injection port 33) enables fluids to be inserted or removed from the tissue specimen retained in the cavity 27. A label 31 with indicia identifying the tissue specimen 13 maybe applied to the top surface 32 of the cassette 10, or along the bottom surface 12a of cassette 10, or both, such as shown in FIGS. 2 and 11. The indicia may represent a bar code or alphanumeric numerals identifying the tissue specimen, such as the patient name, date, physician, or other references to the surgical procedure.

Referring to FIGS. 7–11, the orientation of the tissue specimen 13 on window 16 in a closed cassette will now be described. If prior to closure of cassette 10, the tissue specimen 13 on upper surface 16b of window 16 in aperture 18 extends beyond the top surface 12b of base member 12, membrane 26 compresses the tissue specimen, as shown in FIG. 7. The top of the tissue specimen 13 may be scored prior to the closure of the cassette 10 to facilitate movement of the edges 13a of the tissue specimen 13 toward window 16. One or more scoring incisions along the top surface of the tissue may be needed when the specimen's edges are at a steep angle with respect to the surface of window 16. Such incisions should not extend through the specimen, and may be in a cross-pattern or other pattern which relaxes tension of the tissue such that the tissue edges may be moved to flatten them against window 16.

Figure 9:
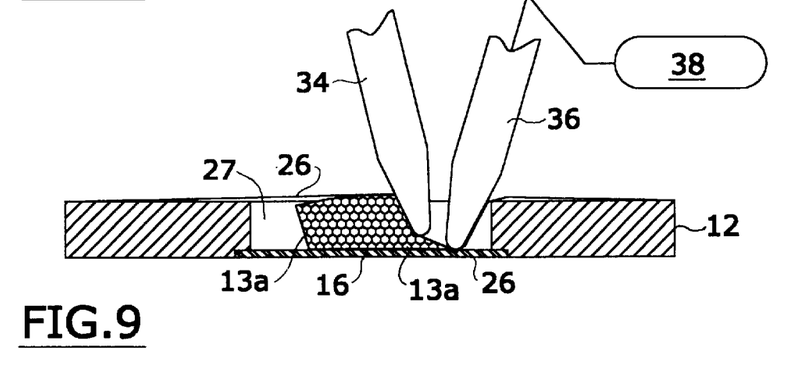
FIG. 9 is a cross-section view similar to FIG. 8 showing an example of a second probe for bonding the membrane and window together at a location to retain the planar orientation of the edge of the tissue specimen.
Figure 10:
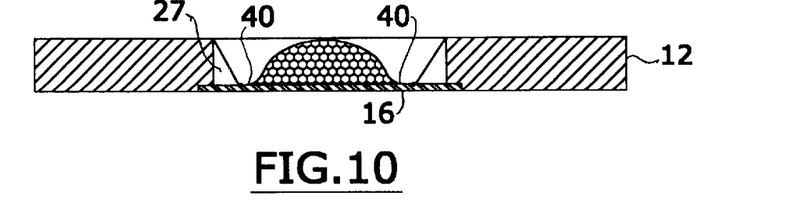
FIG. 10 is a cross-section view similar to FIG. 9 showing an example of the tissue specimen with its edges positioned planar against the window and the membrane bonded to the window at multiple locations around the tissue specimen.

As shown in FIG. 8, a user, such as a physician or trained operator, using a probe 34 manipulates one of the edges 13a of the tissue downwards against the window 16 under the tension of membrane 26, such that the edge is planar with upper surface 16b of window 16. With the edge 13a held in that position, the user manipulates another probe 36 against the membrane 26 in gap 29 until reaching window 16 at a location near the first probe which will hold the edge 13a in the desire position when probe 34 is removed, as shown in FIG. 9. The probe 36 is then actuated by the user to conduct heat though thermal bond actuating means 38 to produce a bond (weld or joint) between the membrane 26 and the window 16 at a point or location 40 (FIG. 10), thereby retaining the edge 13a of the specimen in the desired planar orientation against window 16. Thermal bond actuating means 38 may be similar to a soldering iron operating at a low temperature to weld the material of the plastic membrane and window together without affecting the integrity of the cavity. Other bond actuating means may also be used, such as sonic welding. If needed, more than one bond at different locations 40 in gap 29 may be used to retain edge 14a. This is repeated around the tissue specimen 13 until all of the edges 13a are held in a planar orientation against the window 16 by multiple bonds 40 between membrane 26 and window 16. FIGS. 10 and 11 show multiple bonds 40 retaining the tissue specimen 13 is the desired planar orientation. Probes 34 and 36 have sufficiently blunt ends to avoid puncturing membrane 26 during this procedure. In this manner, tissue specimen 13 is oriented in a closed cassette 10 such that the edges 13a of the tissue specimen are positioned planar against the window 16 and are retained in that position by bonds formed between the membrane 26 and window 16 at multiple points or locations 40 around the tissue specimen.

In the alternative to thermally or sonically formed bonds, a contact adhesive may be applied to the upper surface 16a of window 16 or the surface of membrane 26 facing window 16, or both, prior to placement of the tissue specimen in the cassette, such that probe 36 by contacting membrane 26 to window 16 adhesively bonds them to each other at a point 40. Further, the contact adhesive may be a UV light cure adhesive, such that after the bonds are formed they may be exposed to UV light to harden them.

Figure 12:
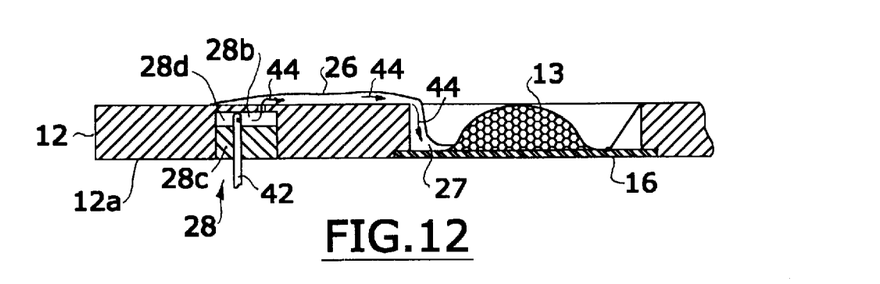
FIG. 12 is a cross-sectional view along line FIG. 12—12 of FIG. 11 showing an example of a syringe needle inserting fluid into the cavity of the cassette through the injection port.

Referring to FIG. 12, a syringe (not shown) with a needle 42 may be inserted into injection port 28 through self-sealing member 28c to force fluid into cavity 27 through passage 28d and channel 28b. Since multiple bonds do not seal tissue specimen 13 within cavity 27, the fluid freely flows to the tissue specimen 13, thereby immersing the tissue specimen in fluid, as shown by arrows 44. The fluid may represent an optical index matching fluid to facilitate imaging of the specimen by an optical imaging microscope. Similarly, the fluid may be withdrawn by the use of a syringe with needle 42 to suction the fluid from cavity 27. The self-sealing member 28c allows the insertion of the needle without compromising the integrity of the cavity 27. Thus, the tissue specimen is retained in the cassette in the desired orientation, while being permeable to fluids inserted through the injection port 28. The fluid inserted flows between the tissue specimen 13 and window 16 due to the elasticity of the membrane 26 and the pressure of the fluid.

Figure 12A:
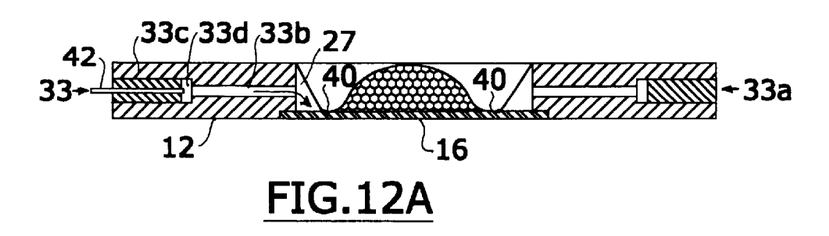
FIG. 12A is a cross-sectional view along line FIG. 12—12 of FIG. 11 showing an example of side injection ports to the cavity of the cassette.

For the side injection port 33 of FIG. 1B, FIG. 12A shows the needle 42 inserted into injection port 33 through self-sealing member 33c to insert fluid to, or withdraw fluid from, cavity 27 through passage 33d and channel 33b. FIG. 12A also shows another side injection port 33a identical to injection port 33, but oriented opposite injection port 33 in base member 12, such that the cassette has two injection ports 33 and 33a . This may facilitate the flow of fluid through cavity 27 by simultaneously inserting a fluid through port 33 and removing the fluid through port 33a, or vise versa. The second injection port 33a may also serve as a backup port if the first injection port 33 fails to function.

Figure 13:
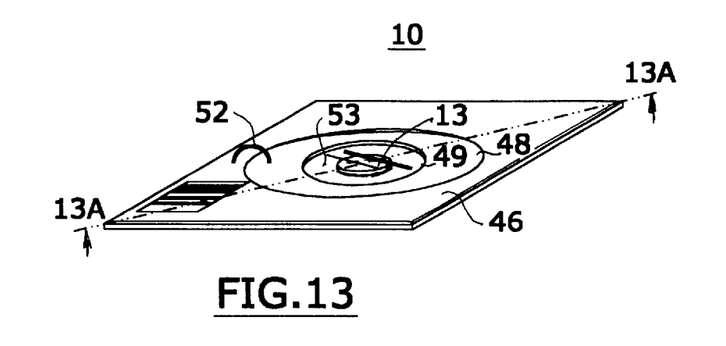
FIG. 13 is a perspective view of the cassette in accordance with another embodiment for sealing the upper member and base member of the cassette together.
Figure 13A:
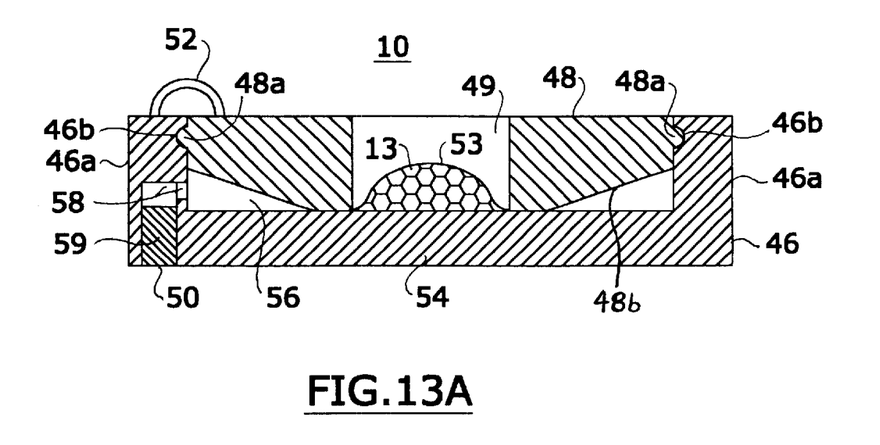
FIG. 13A is cross-sectional view along line 13A—13A of the cassette of FIG. 13.

Referring to FIGS. 13 and 13A, another embodiment is shown for sealing the upper and base members of cassette 10 together. In this embodiment, the base and upper members of cassette 10 are denoted as 46 and 48, respectively, and the base member of FIG. 5 is shown. Base member 46 has an annular wall 46a which extends about its periphery into which the upper member 48 can be received. The upper member 48 has an aperture 49 and an annular ridge or tongue 48a which extends along its outer edge. Upper member 48 is insertable into the base member 46 such that ridge 48a fits into an annular groove 46b of base member 46 along the inside of wall 46a, thereby sealing the upper member 48 to the lower member 46 to define an enclosed cavity 56 between the membrane 53 and the base member 46. The compression of the edges 13a of the tissue specimen orients such edges planar against a window 54, which is defined by the part of the optically transmissive base member 46 below aperture 49 of upper member 48. Upper member 48 is attached to base member 46 by a loop member 52, which may be composed of plastic. Aperture 49 may be sized sufficiently larger that the tissue specimen 13 to enable multiple bonds to be made between membrane 53 and window 54 to hold the edges positioned planar to the window, such as described earlier. Membrane 53 is similar to membrane 26, and injection port 50 is similar to injection port 28 with a self-sealing member 59 and a channel 58 through wall 46a to enable fluids to be insertable and removable from the tissue specimen 13 in cavity 56. Upper member 48 may have circular or disc-like shape with a circular, curved lower surface 48b.

Figure 13B:
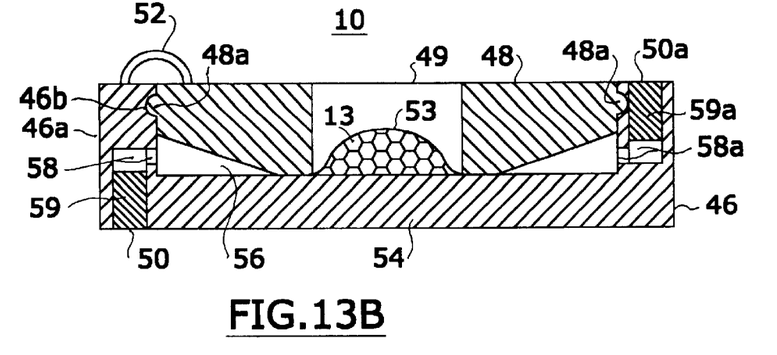
FIG. 13B is cross-sectional view along line 13A—13A of the cassette of FIG. 13 showing two injection ports.
Figure 13C:
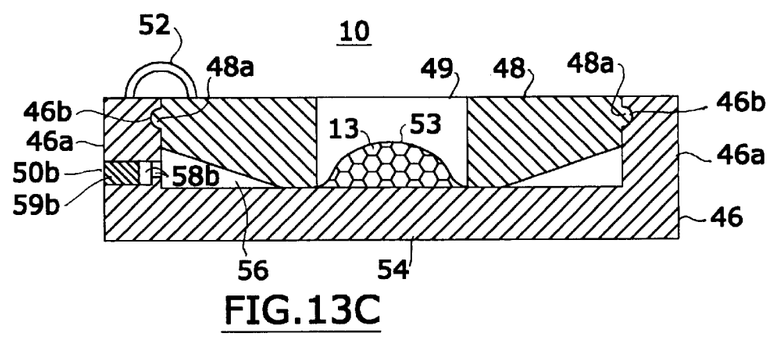
FIG. 13C is cross-sectional view along line 13A—13A of the cassette of FIG. 13 showing an example of a side injection port of FIG. 1C.

Referring to FIG. 13B, in the embodiment shown in FIG. 13, a second injection port 50a may be provided from the top surface of base member 46 in addition to, or instead of, injection port 50. Like injection port 50, injection port 50 has a self-sealing member 59a and a channel 58a through wall 46a to enable fluids, via a syringe needle, to be insertable and removable from the tissue specimen 13 in cavity 56. The two ports 50 and 50a have channels 58 and 58a, respectively, which may be located long opposite sides of base member 46. By providing a cassette 10 with two injection ports, fluid can be simultaneously inserted through one port and removed through the other port to enable a fluid flow through cavity 56. Although only one or two ports are shown, additional number of ports may be similarly provided at different location in the base member. A variation of the injection port 50 and 50a is shown in FIG. 13C in which a side injection port 50b is provided through the side of base member 46. Like injection ports 50 and 50a, injection port 50b has a self-sealing member 59b and a channel 58b through wall 46a to enable fluids, via a syringe needle, to be insertable and removable from the tissue specimen 13 in cavity 56. Multiple ones of side injection port 50b, such as two, may be provided at opposite sides of the base member 46.

Figure 14:
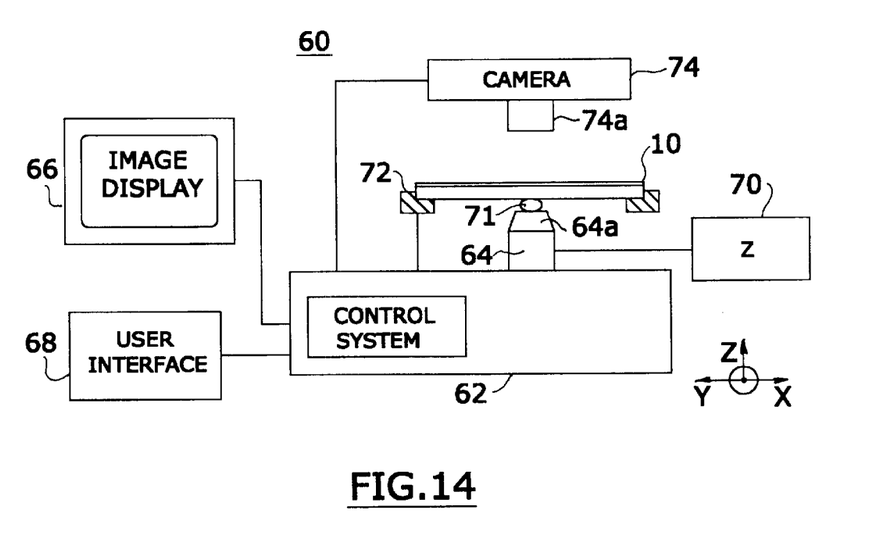
FIG. 14 is a block diagram of a confocal microscope system with a cassette in accordance with the present invention.

Referring to FIG. 14, a confocal imaging system 60 having the cassette 10 is shown. Confocal imaging system 60 includes a computer control system 62 having a confocal imaging head 64 with a liquid immersion objective lens 64a, and a display 66 and user interface 68 coupled to control system 62. The confocal imaging head 64 and control system 62 provides confocal microscopic images of optically sectioned tissue on the display 66 as described, for example, in U.S. Pat. No. 5,788,639, or in published International Patent Application WO 96/21938, which are herein incorporated by reference. The confocal imaging head 64, control system 62, display 66, and user interface 68 may represent a confocal microscope, such as the "VivaScope" manufactured by Lucid, Inc. of Henrietta, N.Y. A z-actuator 70 can move the confocal imaging head 64 (or alternately, only objective lens 64a) in a z direction, via signals from control system 62, to control the depth of imaging in tissue, i.e., the distance of objective. lens 64a to window 16 of cassette 10.

The confocal imaging system 60 further includes an x-y stage 72 which supports cassette 10 and presents the window 16 of the cassette to a liquid immersion objective lens 64a of the confocal imaging head 64. Stage 72 has actuators (not shown) which can move the cassette 10 in x,y orthogonal directions in response to signals from control system 62. User interface 68 may represent a keyboard, mouse, joystick, or combinations thereof, which enable a user, via control system 62, to control the z-actuator 70 and x-y stage 72 such that different parts of the tissue specimen may be imaged by the confocal imaging head 64. Prior to locating the cassette in stage 72, a fluid which is matched to the optical index of the immersion objective lens 64a is inserted into the cavity of the cassette 10 via the injection port 28 or 33. Optionally, an optical coupling fluid 71 may be placed between lens 64a and window 16 of cassette 10 to optically couple the lens 64a to window 16. The fluid 71 may have the same optical index as the fluid inserted in the cavity of cassette 10. The cassette 10 may that than shown in FIGS. 11 or 13.

An optional camera 74 in the confocal imaging system 60 is provided to capture images of the tissue specimen through a lens 74a directed to aperture 20 in upper member 14 of the cassette 10. Camera 74 may be a digital camera which captures still images, or may be a video camera. The control system may also send signals to the camera 74 to control its operation, such as enabling the camera to capture an image or focusing the camera. Signals representing captured images from camera 74 are received by the control system 62.

Figure 15:
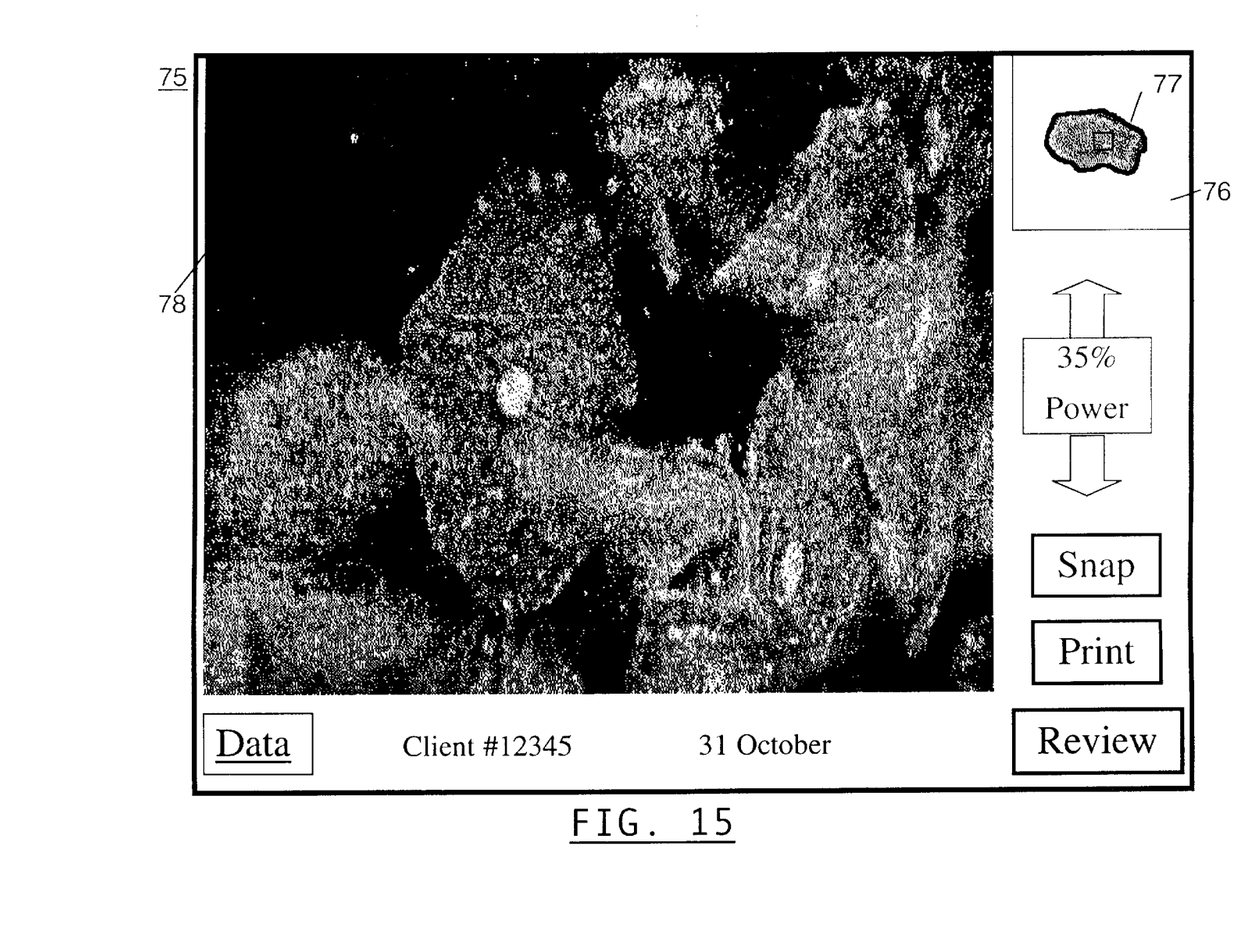
FIG. 15 is an illustration of a screen on the display of the system of FIG. 14 during confocal imaging of a tissue specimen in the cassette.

On display 66 the control system 62 visualizes images of microscopic sections of the tissue specimen from confocal imaging head 64 and macroscopic images from camera 74. FIG. 15 shown an example of a screen (denoted as 75) of display 66 during confocal imaging, where image 76 represents a macroscopic image of a tissue specimen in cassette 10 from camera 74, and image 78 represents an optical section of the tissue specimen imaged through confocal imaging head 64. Image 76 may be maintained on the screen 75 during optical sectioning to guide the user as to the location of microscopic section 78 with respect to the tissue specimen. For example, a box 77 may indicate the relative location of the microscopic image 78 with respect to the macroscopic image 76. The x-y stage 72 is positioned with respect to camera lens 74a such that a marker, such as a cross-hair, may be overlaid by control system 62 on macroscopic image 76 showing the relative location of the confocal imaging head 64 with respect to the tissue specimen. Since the edges of the tissue specimen are planar against window 16 of cassette 10, optical sections imaged on display 66 from along the edges of the tissue specimen can provide information determining whether a tumor is fully contained in the tissue specimen for Mohs surgery. If desired, images of optical sections from different parts of the tissue specimen may be scanned automatically by the control system 62 by controlling the movement of x,y stage 72. The scanned images of optical sections are electronically combined in memory of the control system 62 to provide an optical section having a larger field of view to the user. If imaging by another confocal imaging head is desired, the fluid can be replaced with a different optical index matching fluid, via injection port 28 of the cassette.

Although a confocal imaging head 64 is described herein, other optical imaging techniques may also be used in head 64, such as optical coherence tomography, such as described in Schmitt et al., "Optical characterization of disease tissues using low-coherence interferometry," Proc. of SPIE, Volume 1889 (1993), or a two-photon laser microscope, as described in U.S. Pat. No. 5,034,613.

After imaging of the tissue specimen is complete, the tissue specimen can be removed from stage 72 and archived in cassette 10. To preserve the tissue specimen, a preservative fluid, such as formalin, may be inserted in the cavity of the cassette, via injection port 28, after any fluid in the cavity is removed. The entire cassette with the tissue specimen from Mohs surgery can thus be stored intact with indicia 31 on the cassette referencing the procedure. Optical sectioning of tissue specimens can facilitate their archiving since intact specimens may require less storage space than traditional slides, and can easily be labeled with indicia 31 on the cassette.

Figure 16:
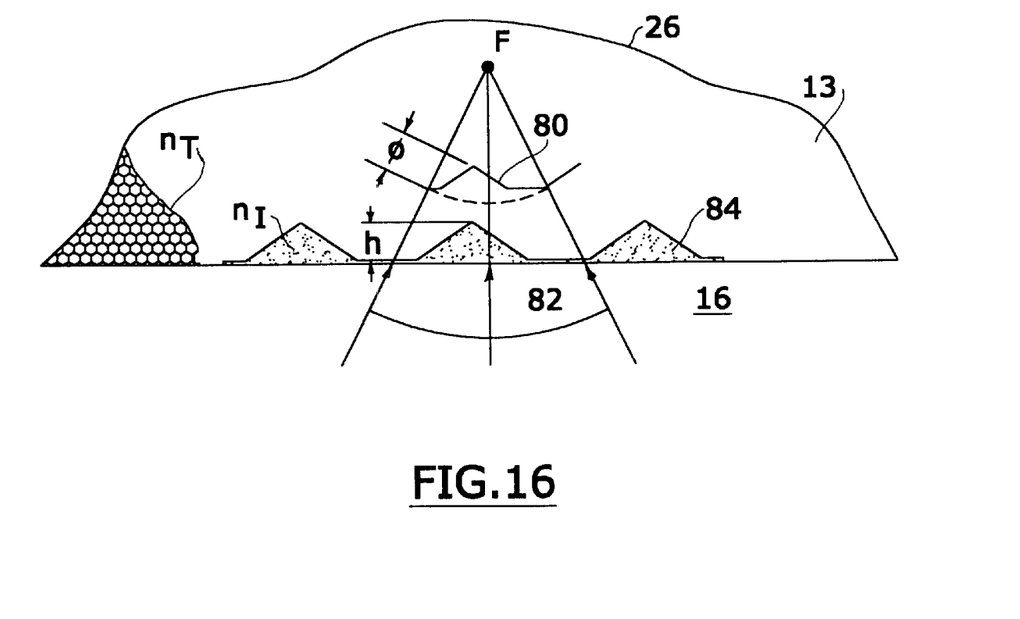
FIG. 16 is an enlarged view illustrating the corrugations formed between a tissue specimen and the window of the cassette.

The particular immersion fluid inserted through an injection port into the cavity of the cassette 10 containing the tissue specimen 13 may be selected as follows to enhance imaging. Surface corrugations at the interface between the tissue specimen 13 and the window 16 are filled with the immersion fluid, which produces optical corrugations in the wavefront of the beam focused into the specimen. These corrugations reduce the fidelity of the images. The effect of the corrugations can be reduced by matching the refractive index of the immersion liquid with the tissue. As shown in FIG. 16, the corrugations due to the surface texture of the specimen 13 creates corrugations having a depth (h) (from the apex of the corrugation peaks to the bottom of the valleys of the corrugations) which may be approximately 200 microns in length. The index of refraction of the tissue is $n_T$, while the index of refraction of the immersion fluid, which fills the corrugations providing the surface texture of the specimen 13, have an index $n_I$. The beam is focused at a focus f in the section to be imaged. The wavefront which may be spherical, can be distorted due to an optical path difference φ imprinted on the wavefront which converges to the focus F. This path difference is a function of the product of the corrugation height h and the difference between $n_T$ and $n_I$. The use of the index matching fluid reduces the optical path difference so that the imprint is minimized. The optical path difference φ is shown enlarged at 80 in FIG. 16. This optical path difference may also be viewed as the wavefront which is propagating to the focus F. This wavefront may be spherical and part of a sphere as shown at 82 prior to passing through corrugations at the surface of the specimen 13. The optical path distortion after transmission through the tissue surface is approximated by the relation (φ=h($n_T$−$n_I$), where h is the mechanical depth of surface texture. In order to correct for the distortion of the beam wavefront (which may be a spherical wavefront) by virtue of the variation in index of refraction presented by corrugations, it is desirable that the difference in index of the immersion liquid 84 and the average index of refraction of the tissue multiplied by the corrugation height h that is the optical path distance between the hills and valleys of the corrugation), not exceed a quarter wavelength of the laser beam which is used for imaging by the imaging system 62. Thus, the immersion medium 84 is selected for the tissue type which is placed in the cassette and substantially corrects for optical distortion due to the surface texture of the tissue specimen.

From the foregoing description, it will be apparent that there has been provided a cassette for facilitating optical sectioning of a retained tissue specimen. Variations and modifications in the herein described cassette, method, and system in accordance with the invention will undoubtedly suggest of themselves to those skilled in the art. Accordingly, the foregoing description should be taken as illustrative and not in a limiting sense.

What is claimed is:

1. A cassette for enabling optical imaging of a surgically exposed tissue specimen having edges comprising:
   a base member having an optically transparent window;
   a membrane locatable over a substantial portion of said base member including said window; and an upper member in which when a tissue specimen is located on said window, said upper member locates said membrane over said base member to produce an enclosed cavity between said membrane and said window having said tissue specimen therein, in which said membrane is sufficiently pliable to be capable of contacting said window at one or more locations.

2. The cassette according to claim 1 wherein said upper member comprise an aperture to enable said tissue specimen to be observable through said membrane via said aperture when the tissue specimen is located on said window said upper member locates said membrane over said base member to produce an enclosed cavity between the membrane and the window.

3. The cassette according to claim 1 wherein said tissue specimen is viewable through said window when the tissue specimen is located in the enclosed cavity between the membrane and the window.

4. The cassette according to claim 1 wherein said tissue specimen is positionable through said membrane when the tissue specimen is located in the enclosed cavity.

5. The cassette according to claim 1 wherein said base member further comprises an upper surface facing said upper member and an aperture extending through said upper surface within which said window is located.

6. The cassette according to claim 1 wherein said base member is composed of an optically transparent material providing a window upon which the specimen is situated.

7. The cassette according to claim 1 wherein said base member further comprises at least one injection port through which liquids are injectable and removable from said cavity.

8. The cassette according to claim 7 wherein said injection port comprises an opening having a self-sealing member and a channel from the opening into the cavity.

9. The cassette according to claim 7 wherein said injection port is located through the bottom or side of said base member.

10. The cassette according to claim 1 further comprising means for coupling said upper and base members to each other to enable said upper and base members to be positionable in an open state to allow placement of a tissue specimen upon the window of said base member, and then in a closed state wherein said upper member covers said base member to form the cavity between said membrane and said window retaining said tissue specimen therein.

11. The cassette according to claim 10 wherein said means further couples one side of said membrane to enable said membrane to be maintained between said upper and base members.

12. The cassette according to claim 1 wherein said window is rigid.

13. The cassette according to claim 1 wherein said upper member has a surface and an aperture extending through said surface and said membrane has an outer edge attachable to said surface of said upper member.

14. The cassette according to claim 1 wherein said membrane is a thin layer of plastic.

15. The cassette according to claim 1 further comprising means for sealing said base member and said upper member together to define the enclosed cavity therein.

16. The cassette according to claim 1 further comprising means for sealingly engaging the upper member to the lower member to form a hermetic seal to define the cavity between said membrane and said window.

17. The cassette according to claim 1 wherein said upper member has a lower surface and said base member has an upper surface which faces said lower surface of said upper member when said upper member covers said base member to form a cavity capable of retaining a tissue specimen between the membrane and the window.

18. The cassette according to claim 1 wherein said upper member has a continuous outer edge, and said base member has a continuous side wall into which said upper member is received, and said cassette further comprises means provided by said upper and base members to couple said outer edge of said upper member along the side wall of the base member to form a cavity capable of retaining a tissue specimen between the membrane and the window.

19. The cassette according to claim 1 further comprising a label having indicia.

20. The cassette according to claim 1 wherein said tissue specimen in said cassette is imagable through said window by a confocal microscope.

21. The cassette according to claim 1 wherein said tissue specimen in said cassette is imagable through said window by an imaging system operating in accordance with one of two photon microscopy or optical coherence tomography.

22. The cassette according to claim 1 further comprising a fluid in said cavity having an index of refraction substantially matching that of the tissue specimen.

23. The cassette according to claim 1 further comprising a fluid in said cavity which substantially corrects for optical distortion due to the surface texture of the tissue specimen.

24. The cassette according to claim 1 wherein at least one of said base member or said upper member has indicia identifying the tissue specimen.

25. The cassette according to claim 24 wherein said indicia represents one of a bar code or alphanumeric.

26. A cassette for enabling optical imaging of a surgically exposed tissue specimen having edges comprising:
   a base member having an optically transparent window;
   a pliable membrane locatable over a substantial portion of said base member including said window; and
   an upper member in which when a tissue specimen is located on said window, said upper member locates said membrane over said base member to produce an enclosed cavity between said membrane and said window having said tissue specimen therein, wherein said tissue specimen has at least one edge positionable through said membrane planar against said window when the tissue specimen is located in the enclosed cavity, and said cassette further comprises at least one bond formed between said membrane and said window to retain said edge of the tissue specimen planar against said window.

27. A cassette for enabling optical imaging of a surgically exposed tissue specimen having edges comprising:
   a base member having an optically transparent window;
   a pliable membrane locatable over a substantial portion of said base member including said window;
   an upper member in which when a tissue specimen is located on said window, said upper member locates said membrane over said base member to produce an enclosed cavity between said membrane and said window having said tissue specimen therein, wherein said upper member has an aperture;
   a gap around said tissue specimen observable through said aperture when the tissue specimen is within said enclosed cavity; and
   a plurality of bonds connecting said membrane and said window at locations in the gap to retain the edges of the tissue specimen planar against said window.

28. A cassette for enabling optical imaging of a surgically exposed tissue specimen having edges comprising:

a base member having an optically transparent window;

a pliable membrane locatable over a substantial portion of said base member including said window;

an upper member in which when a tissue specimen is located on said window, said upper member locates said membrane over said base member to produce an enclosed cavity between said membrane and said window having said tissue specimen therein;

at least one injection port in said base member; and means for forming one or more bonds connecting said membrane and said window to retain the tissue specimen in a certain orientation while enabling said tissue specimen to receive fluid inserted via said injection port.

29. A method for using a cassette for preparing a tissue specimen for examination by a confocal microscope or other optical imaging microscope comprising the steps of:

locating a tissue specimen on an optically transparent window of a base member;

placing a pliable optically transparent membrane over at least a substantial portion of said base member including said window;

sealingly engaging the membrane to the base member to produce a cavity between said membrane and said window;

positioning edges of the tissue specimen against the window; and fixing the location of the edges positioned against the window by connecting the membrane to the window at multiple points.

30. The method according to claim 29 further comprising the step of inserting a fluid into said cavity through said base member through an injection port in the base member.

31. The method according to claim 29 further comprising the step of: imaging said tissue specimen through said window.

32. The method according to claim 31 wherein said imaging step is enabled by one of confocal microscopy, two-photon microscopy, or optical coherence tomography.

33. The method according to claim 29 further comprising the step of locating a fluid in said cavity having an index of refraction substantially matching that of the tissue specimen.

34. The method according to claim 29 further comprising the step of locating a fluid in said cavity which substantially corrects for optical distortion due to the surface texture of the tissue specimen.

35. The method according to claim 29 further comprising the step of providing indicia identifying said tissue specimen.

36. A system for enabling optical imaging of a surgically exposed tissue specimen having edges comprising:

a cassette having a base member having an optically transparent window upon which said tissue specimen is locatable, a membrane locatable over a substantial portion of said base member including said window, and an upper member which locates said membrane over said base member to produce an enclosed cavity between said membrane and said window having said tissue specimen when said tissue specimen is located on said window of said base member;

means for locating each of the edges of the tissue specimen planar against said window through said membrane; and means for producing a plurality of bonds between said membrane and said window at locations around said tissue specimen to retain said tissue specimen against said window when each of said edges of the tissue specimen are located planar on said window of said base member.

37. The system according to claim 36 further comprising means in said cassette for inserting fluid to the cavity.

38. The system according to claim 37 wherein said fluid substantially corrects for optical distortion due to the surface texture of the tissue specimen.

39. The system according to claim 37 wherein said means for inserting fluid further provides means for removing said fluid.

40. The system according to claim 36 further comprising a fluid in said cavity having an index of refraction substantially matching that of the tissue specimen.

41. A cassette for a tissue specimen comprising:

a first member having an optically transparent window on which said tissue specimen is locatable;

a second member providing a thin layer of material locatable over at least a substantial portion of said first member including said window in which said second member is sufficiently pliable to be capable of contacting said window at one or more locations;

a third member having a surface and an aperture extending through said surface; and means for engaging said third member to said first member when said second member is located over said first member to form a cavity between said second member and said window when the tissue specimen is located on said window, wherein said tissue specimen is observable through both said window and said second member via said aperture of said third member.

42. The cassette according to claim 41 wherein said engaging means attaches said first and third members to each other along the periphery of said first and third members.

43. A system for optically imaging sections of a tissue specimen comprising:

a cassette having a window and means for applying pressure onto said tissue specimen to retain said tissue specimen against said window; and imaging means directed to said tissue specimen through said window to produce images representing one or more sections of said tissue specimen, wherein said imaging means represent a microscopic imaging means to provide microscopic images of sections of the tissue specimen, said cassette has a base member with said window and an upper member having an aperture through which said tissue specimen is viewable, and said system further comprises means for producing macroscopic images of the tissue specimen imaged through said aperture of said cassette.

44. The system according to claim 43 wherein said imaging means is a confocal microscope.

45. The system according to claim 44 wherein said confocal microscope has an objective lens, and said system further comprises a fluid between said objective lens and window of the cassette which optically couples the objective lens to the window.

46. The system according to claim 43 wherein said imaging means is operative by one of optical coherence tomography and two-photon microscopy.

47. The system according to claim 43 further comprising a movable stage to support said cassette with respect to said imaging means.

48. The system according to claim 43 further comprising a control system coupled to said microscopic imaging means and macroscopic imaging means which provides on a display coupled to said control system a screen having at least said microscopic image and macroscopic image of the tissue specimen.

49. The system according to claim 43 wherein said cassette has means for enabling a fluid to be inserted.

50. The system according to claim 49 where in said fluid has an index of refraction which substantially matches the index of refraction of the tissue specimen.

51. The system according to claim 43 wherein said tissue specimen in said cassette is obtained from a patient through Mohs surgery.

* * * * *